(12) United States Patent
Deeb et al.

(10) Patent No.: US 10,015,969 B2
(45) Date of Patent: Jul. 10, 2018

(54) METHOD FOR THE REMOVAL AND CONTROL OF ARTHROPOD INFESTATION IN INTERIOR DWELLINGS

(71) Applicant: MARIA BEUG-DEEB INC., Roswell, GA (US)

(72) Inventors: Thomas M. Deeb, Roswell, GA (US); Maria U. D. Beug-Deeb, Roswell, GA (US)

(73) Assignee: Maria Beug-Deeb, Roswell, GA (US)

( * ) Notice: Subject to any disclaimer, the term of this patent is extended or adjusted under 35 U.S.C. 154(b) by 0 days.

(21) Appl. No.: 14/025,859

(22) Filed: Sep. 13, 2013

(65) Prior Publication Data
US 2014/0073605 A1   Mar. 13, 2014

Related U.S. Application Data

(60) Provisional application No. 61/700,412, filed on Sep. 13, 2012.

(51) Int. Cl.
| | |
|---|---|
| A01N 65/00 | (2009.01) |
| A01P 7/04 | (2006.01) |
| A01N 53/00 | (2006.01) |
| A01M 7/00 | (2006.01) |
| A01N 25/00 | (2006.01) |
| A01N 25/30 | (2006.01) |
| A01M 1/20 | (2006.01) |
| A01M 1/24 | (2006.01) |
| A01M 19/00 | (2006.01) |
| A47L 11/34 | (2006.01) |

(52) U.S. Cl.
CPC ........... *A01N 53/00* (2013.01); *A01M 1/2094* (2013.01); *A01M 1/245* (2013.01); *A01M 7/00* (2013.01); *A01M 19/00* (2013.01); *A01N 25/00* (2013.01); *A01N 25/30* (2013.01)

(58) Field of Classification Search
CPC ..... A01M 1/2094; A01M 1/245; A01N 25/00; A01N 25/30
See application file for complete search history.

(56) References Cited

U.S. PATENT DOCUMENTS

| | | | |
|---|---|---|---|
| 125,557 | A | 4/1872 | Ewing |
| 601,168 | A | 3/1898 | Priest |
| 2,565,471 | A | 8/1951 | Buntin et al. |
| 3,964,925 | A | 6/1976 | Burgoon |
| 4,168,563 | A | 9/1979 | O'Bryan |
| 4,397,859 | A * | 8/1983 | Geering .......................... 514/67 |
| 4,448,330 | A | 5/1984 | Roux |
| 4,490,270 | A | 12/1984 | Hackett et al. |
| 4,735,939 | A | 4/1988 | McCoy et al. |
| 4,843,752 | A | 7/1989 | Munemasa et al. |
| 5,004,557 | A | 4/1991 | Nagarajan et al. |
| 5,114,574 | A | 5/1992 | Barry |
| 5,151,181 | A | 9/1992 | Barry |
| 5,284,597 | A | 2/1994 | Rees |
| 5,314,699 | A | 5/1994 | Baden |
| 5,338,475 | A | 8/1994 | Corey et al. |
| 5,360,609 | A * | 11/1994 | Wellinghoff ............... 514/772.3 |
| 5,432,975 | A | 7/1995 | Hilmanowski |
| 5,492,540 | A | 2/1996 | Leifheit et al. |
| 5,534,167 | A | 7/1996 | Billman |
| 5,555,598 | A | 9/1996 | Grave et al. |
| 5,587,221 | A | 12/1996 | McCamy |
| 5,589,080 | A | 12/1996 | Cho et al. |
| 5,802,664 | A | 9/1998 | Mondigo et al. |
| 5,839,155 | A | 11/1998 | Berglund et al. |
| 6,010,539 | A | 1/2000 | Del Pesco |
| 6,055,699 | A | 5/2000 | Cho |
| 6,076,229 | A | 6/2000 | Berglund |
| 6,106,182 | A | 8/2000 | Hamm et al. |
| 6,645,949 | B1 | 11/2003 | Nigg et al. |
| 7,150,068 | B1 | 12/2006 | Ragner |
| 7,171,722 | B2 | 2/2007 | Keller |

(Continued)

FOREIGN PATENT DOCUMENTS

| | | |
|---|---|---|
| JP | 3015831 B2 | 12/1995 |
| JP | 3550138 B2 | 8/2004 |

(Continued)

OTHER PUBLICATIONS

Purdue, "Bed Bugs", http://extension.entm.purdue.edu/publichealth/insects/bedbug.html, Sep. 26, 2009.*
Hill, "Siloxane surfactants: Specialist Surfactants", Blackie Academic and Professional: London, pp. 143-168, 1997.*
Miller, "Bed Bug Treatment Using Insecticides", https://web.archive.org/web/20100814074303/http://www.vdacs.virginia.gov/pesticides/pdffiles/bb-treatment1.pdf, Aug. 6, 2010.*
ICF Consulting for the USDA National Organic Program, "Chlorine/Bleach", Technical Evaluation Report, pp. 1-13, Jan. 6, 2006.*
Aqualux, webpage at www.aqualuxcarpentcleaning.com [retrieved on Feb. 12, 2015], retrieved from the Internet: <URL: http://www.aqualuxcarpetcleaning.com/tips/dont-let-the-bed-bugs-bite/>, Oct. 3, 2010.*
Modern Pest Control, "Information About Bed Bugs", Mar. 11, 2010, 5 pages.*
DuPont, "DuPont™ Zonyl® Fluorosurfactants", 6 page, 2007 [brochure].*
PCT/US2013/059581 International Search Report dated Jan. 2, 2014.

(Continued)

*Primary Examiner* — Robert T. Crow
*Assistant Examiner* — John P Nguyen
(74) *Attorney, Agent, or Firm* — David W. Ladner; Ladner Patent Management LLC

(57) ABSTRACT

There is provided a method for the removal and control of arthropod infestation comprising the cleaning of surfaces and objects within an interior dwelling space using a high efficiency water extraction device, utilizing water that is heated to a temperature sufficient to kill the pest, and to which is added a cleaning agent comprising a surfactant that imparts a surface tension of between about 15 and about 30 dynes/cm, (a "super wetting agent"); in combination with application of an effective arthropod control composition to surfaces and objects within the interior dwelling spaces, the arthropod control composition comprising an arthropod control agent and a surfactant that imparts a surface tension of below about 30 dynes/cm.

8 Claims, No Drawings

(56) References Cited

U.S. PATENT DOCUMENTS

| | | | |
|---|---|---|---|
| 7,310,855 | B2 | 12/2007 | Blocker et al. |
| 7,353,563 | B2 | 4/2008 | Blocker et al. |
| 7,386,915 | B2 | 6/2008 | Blocker et al. |
| 7,617,564 | B2 | 11/2009 | Stuthers et al. |
| 7,624,474 | B1 | 12/2009 | Cho |
| 7,627,927 | B2 | 12/2009 | Blocker et al. |
| 7,690,148 | B2 | 4/2010 | Hedman |
| 7,727,734 | B1 | 6/2010 | Smith |
| 7,743,552 | B2 | 6/2010 | Borth et al. |
| 7,761,955 | B1 | 7/2010 | Hiltz |
| 7,829,551 | B2 | 11/2010 | Ansell |
| 7,892,528 | B2 | 2/2011 | Siljander et al. |
| 7,905,048 | B2 | 3/2011 | Borth et al. |
| 7,926,222 | B2 | 4/2011 | Molnar et al. |
| 8,020,252 | B2 | 9/2011 | Blocker et al. |
| D648,819 | S | 11/2011 | Bronk |
| 8,056,182 | B2 | 11/2011 | Day |
| 8,097,602 | B1 | 1/2012 | Holzer |
| 2002/0011584 | A1* | 1/2002 | Uchiyama ............... C11D 1/62 252/8.91 |
| 2003/0013683 | A1* | 1/2003 | Holzer ........................... 514/63 |
| 2004/0171511 | A1 | 9/2004 | Nagai et al. |
| 2005/0107276 | A1* | 5/2005 | Merritt et al. ............... 510/278 |
| 2006/0090286 | A1 | 5/2006 | Day |
| 2006/0248677 | A1 | 11/2006 | Cho |
| 2007/0196412 | A1 | 8/2007 | Karl et al. |
| 2007/0266749 | A1 | 11/2007 | Rader et al. |
| 2007/0283986 | A1 | 12/2007 | Baum |
| 2009/0043133 | A1* | 2/2009 | Murphy et al. ............... 568/683 |
| 2009/0145019 | A1 | 6/2009 | Nolan et al. |
| 2010/0120652 | A1 | 5/2010 | Corrado |
| 2010/0166818 | A1 | 7/2010 | Troutman |
| 2010/0205767 | A1 | 8/2010 | Lewis |
| 2011/0213038 | A1 | 9/2011 | Bedoukian |
| 2011/0219665 | A1 | 9/2011 | Hedman |
| 2011/0256196 | A1 | 10/2011 | Lloyd et al. |
| 2011/0289824 | A1 | 12/2011 | Wu et al. |
| 2013/0143832 | A1 | 6/2013 | Sakamoto et al. |

FOREIGN PATENT DOCUMENTS

| | | | |
|---|---|---|---|
| WO | WO2002074088 | A1 | 9/2002 |
| WO | WO2005070210 | A1 | 8/2005 |
| WO | WO2009117621 | A1 | 9/2009 |
| WO | WO2010018360 | A1 | 2/2010 |
| WO | WO2010115065 | A2 | 10/2010 |
| WO | WO2011005325 | A1 | 1/2011 |

OTHER PUBLICATIONS

NJ Dept. of Health and Senior Services, Bed Bug Fact Sheet, Department of Health, P.O. Box 360, Trenton, NJ (USA) Copyright State of New Jersey, 1996-2013.

Bowles, "How to Kill Bed Bugs with Steam", eHow article, Demand Media, Inc., http://www.ehow.com/how_4900053_kill-bed-bugs-steam.html, accessed Jan. 14, 2014; Copyright 1999-2013.

Wang et al., Bed Bug Infestations in an Urban Environment, Emerging Infectious Diseases, 11(4) 523-538, Apr. 2005.

Doggett, A Code of Practice for the Control of Bed Bug Infestations in Australia (Draft), Australian Environmental Pest Managers Association, Bed Bug Code of Practice Working Party, Oct. 20, 2005, Westmead NSW, Australia.

Don't the the Bed Bugs Bite:, Enviornmental Health and Protecion , Lexington-Fayette County Health Department, Lexington, KY, Sep. 2006. www.lexingtonhealthdepartment.org/Portals/0/environmental%20health/bed_bugs_brochure_web.pdf, accessed Jan. 14, 2014.

Jacobs, "Bed Bugs," Entomological Notes, PH-1, College of Agricultural Science, Pennsylvania State University and U.S. Department of Agriculture, Apr. 2003, rev. Jul. 2007.

"Bed Bugs Guide: Steam Cleaning," www.bedbugsguide.com/steam-cleaning-bedbugs.htm, Copyright 2007, Bedbugsguide.com.

Potter, "Bed Bugs", UK Cooperative Extension Service, Univ. of Kentucky, Entfact 646, www2.ca.uky.edu/entomology/entfacts/entfactpdf/ef636.pdf, accessed Jan. 14, 2014, revised Aug. 2008.

Ogg, "Managing Bed Bugs", University of Nebraska Extension publication in Managing Bed Bugs Resource 263, updated on Apr. 5, 2010.

Centers for Disease Control and Prevention and U.S. Environmental Protection Agency. Joint statement on bed bug control in the United States from the U.S. Centers for Disease Control and Prevention (CDC) and the U.S. Environmental Protection Agency (EPA). Atlanta: U.S. Department of Health and Human Services; 2010.

"Bedbugs make a comeback; high-temperature steam the most effective weapon", Press release, Personal Touch Carpet Cleaning, 3852 Norwood Drive #4,Littleton, CO 80125, May 26, 2010.

Miller et al., "Bed Bug Biology and Behavior", Fact Sheets, Virginia Department of Agriculture and Consumer Services, http://www.vdacs.virginia.gov/pesticides/pdffiles/bb-biology1.pdf, accessed Jan. 31, 2014.

"Bed Bugs", Pests in Gardens and Landscapes: Quick Tips, U. of California ANR, published Jun. 2011; www.ipm.ucdavis.edu/PDF/QT/qtbedbugs.pdf,accessed Jan. 14, 2014.

Schulz, Battling the Bedbug Epidemic, Chemical and Engineering News, 89 (10), 13-8, Mar. 7, 2011.

"How to Kill Bed Bugs in Carpet", http://www.whatdobedbugslooklike.net/how-to-kill-bed-bugs-in-carpet.html, accessed Jan. 14, 2014, copyright 2014 Whatdobedbugslooklike.net—Apr. 2, 2011.

Martin et al., "Don't Let the Bed Bugs Bite Into Your NOI", Journal of Property Management, Jul.-Aug. 2011, 76 4, 38-43, Copyright 2011 National Association of Realtors ISSN: 0022-3905.

"Housekeeping Procedures for Bed Bugs", Pest Management; Bed Bugs, Office of Environmental Health and Safety Management, Indiana University, 1514 East Third Street, Bloomington, Indiana 47401, Copyright 2012.

Borel, Will we ever get rid of bedbugs, BBC Future, Oct. 19, 2012, www.bbc.com/future/story/20121019-will-we-ever-get-rid-of-bedbugs, accessed Jan. 14, 2014.

Miller, "Bed Bug Prevention Methods", Fact Sheets, Virginia Department of Agriculture and Consumer Services, http://www.vdacs.virginia.gov/pesticides/pdffiles/bb-prevention1.pdf, accessed Jan. 14, 2014.

Miller, "Using Heat to Kill Bed Bugs", Department of Entomology at Virginia Tech, webpage at www.vdacs.virginia.gov_pesticides_pdffiles_bb-heat1 [retrieved on Apr. 1, 2015]., see p. 1, paragraph 5 and p. 6, last paragraph.

Kells, et al., Temperatures and Time Requirement for Controlling Bed Begs (Cimex lectularius) under Commercial Heat Treatment Conditions, Insects, 2011, 2, 412-422; see p. 417, first paragraph.

Ullah, A., "What is Your Cleaning Temperature", Cleancare Australia, webpage at http://www.cleancare.com.au/what-is-your-cleaning-temperature/w1/i1015454/ [retrieved on Apr. 1, 2015].

United States Environmental Protection Agency, "Controlling Bed Bugs Using Integrated Pest Management (IPM)", webpage at http://www2.epa.gov/bedbugs/controlling-bed-bugs-using-integrated-pest-management-ipm [retrieved on Apr. 9, 2015].

Sutherland, Pest Notes, Publication 7454, University of California Agriculture and Natural Resources, May 2013; see p. 1, paragraph 8, line 6.

Miller, "Non-Chemical Bed Bug Management", Department of Entomology at Virginia Tech, webpage at http://www.vdacs.virginia.gov/pesticides/pdffiles/bb-nonchemical1.pdf [retrieved on Apr. 1, 2015] see p. 2, paragraph 3, line 6.

"Bed Bugs—Importance, Biology, and Control Strategies" Armed Forces Pest Management Board, Technical Guide No. 44, Aug. 2006, see p. 7, "Physical Removal".

"Fact Sheet: Bed Bugs", Washtenaw County Public Health, Ypsilanti, MI, revised 12/10, webpage at http://www.ewashtenaw.org/government/departments/public_health/disease_control/cd_fact_sheets/bedbugs.pdf [retrieved on Apr. 2, 2015], see p. 2, paragraph 4.

Merchant, "Bed bugs: Do-it-yourself control options", Texas A&M University, AgriLife Extension Service, factsheet; webpage at http://

(56) References Cited

OTHER PUBLICATIONS citybugs.tamu.edu/factsheets/biting-stinging/others/ent-3012/ [retrieved Apr. 2, 2015], see p. 2, paragraph 5, line 5.

United States Environmental Protection Agency, "Risk Management Decisions for Individual N-methyl Carbamate Pesticides", webpage at http://www.epa.gov/pesticides/cumulative/carbamate_risk_mgmt.htm [retrieved Apr. 2, 2015].

Chameides, "Is Propoxur the Way to Not Let the Bedbugs Bite?", webpage at http://blogs.nicholas.duke.edu/thegreengrok/bedbugs_post/ [retrieved Apr. 2, 2015].

United States Environmental Protection Agency, "Pesticides to Control Bed Bugs", webpage at http://www2.epa.gov/bedbugs/pesticides-control-bed-bugs#pyrethrins [retrieved Apr. 7, 2015].

European Search Report, re: EP application 13836273, dated Apr. 25, 2016.

Hinson, K.R., et al., "Egg Hatch Rate and Nymphal Survival of the Bed Bug (Hemiptera: Cimicidae) After Exposure to Insecticide Sprays," Journal of Economic Entomology, 109(6), 2016, 2495-2499.

Singh, N., et al., "[Bed Bug Supplement] Natural Pesticides for Bed Bug Control: Do They Work?", PCT Magazine Mar. 26, 2013; On Line article: http://www.pctonline.com/article/pct0313-biopesticides-testing-bed-bugs/ Acessed Oct. 11, 2017.

Snell, E, et al., "Evaluation of the T&M IPM Methods for the Control of Bed Bugs (*Cimex lectularius*)" Jun. 30, 2017, Snell Scientifics, LLC, Meansville, GA, USA.

United States Environmental Protection Agency, Prevention, Pesticides and Toxic Substances (7508C), EPA 738-F-99-010, Sep. 1999.

\* cited by examiner

METHOD FOR THE REMOVAL AND CONTROL OF ARTHROPOD INFESTATION IN INTERIOR DWELLINGS

CROSS REFERENCE TO RELATED APPLICATION

This application claims the benefit of U.S. Provisional Application No. 61/700,412 filed on Sep. 13, 2012, which is incorporated herein by reference in its entirety.

FIELD OF THE INVENTION

This application relates to methods that are useful for the control of arthropod pests, e.g., insect and spider infestations, in interior dwelling spaces.

BACKGROUND OF THE INVENTION

The ability to control infestations of arthropod pests in dwellings occupied by humans is important for several reasons, including providing a healthy environment, protecting humans and pets from harmful effects, i.e., bites or disease, and protecting property from damage and deterioration. In particular, highly infested properties may become uninhabitable and thus suffer a severe decrease in value as a result.

For example bed bugs, or *Cimex lectularius* have long been a pest of interior dwellings occupied by mammals, and numerous methods for their control have been disclosed. This insect feeds on mammalian, e.g., human, blood and often inflicts painful bites in so doing. A recent increase in infestations of this insect has been reported, and with it, an increase desire to find more effective ways to control this noxious pest.

In Mar. 7, 2011, an article (W. G. Schulz, *Chemical and Engineering News*, 89, (10), p. 13-18, entitled "Battling the Bedbug Epidemic", points out that current methods for control infestations are failing. This is in part due to the ban on older insecticides such as DDT, the development of pesticide resistance among bed bugs to currently registered insecticides, and hesitancy to use newer replacement insecticides because of concerns about their human toxicity, particularly to children.

Furthermore, use and misuse of pesticides in the home have resulted in explosions and fire from aerosols, the further scattering of bed bugs to nearby residences from the use of bug bombs, and medical treatment to children exposed to Malathion from its improper use. In addition, the use of ineffective and potentially dangerous home remedies has been reported, despite a lack of any data supporting their efficacy.

The current recommendations involve integrated pest management (IPM), i.e., the use of chemicals together with preventative measures such as monitoring, cleaning and removal of clutter. Detailed descriptions of IPM methods for bed bugs are discussed by various government and university extension agents, as well as exterminating and steam cleaning companies. Examples of these are listed below.
(1) Barb Ogg, University of Nebraska Extension "Managing Bed Bugs", publication in Managing Bed Bugs Resource 263 was updated on Apr. 5, 2010,
(2) NJ Department of Health and Senior Services, Bed Bug Fact Sheet, Department of Health, P.O. Box 360, Trenton, N.J. 08625-0360; Copyright State of New Jersey, 1996-2013.
(3) Steven B. Jacobs, Entomological Notes, Bed Bugs, College of Agricultural Sciences and U.S. Department of Agriculture., and Pennsylvania Counties Cooperating, April 2003, rev. July 2007.
(4) Centers for Disease Control and Prevention and U.S. Environmental Protection Agency. Joint statement on bed bug control in the United States from the U.S. Centers for Disease Control and Prevention (CDC) and the U.S. Environmental Protection Agency (EPA). Atlanta: U.S. Department of Health and Human Services; 2010.
(5) Office of Environmental Health and Safety Management, Indiana University, 1514 East Third Street, Bloomington, Ind. 47401, "Housekeeping Procedures for Bed Bugs", Pest Management; Bed Bugs, Copyright 2013 The Trustees of Indiana University.

Carpet cleaning companies disclose similar methods, focusing on steam cleaning of mattresses, drapes, upholstery and carpeting.

See for example,
(6) "Bedbugs make a comeback; high-temperature steam the most effective weapon", Press release, Personal Touch Carpet Cleaning, 3852 Norwood Drive #4 Littleton, Colo. 80125, Copyright 2013.
(7) Bowles, Donella, "How to Kill Bed Bugs with Steam", eHow article, Copyright 1999-2013 Demand Media, Inc.
(8) "Bed Bugs Guide: Steam Cleaning," Copyright 2007, Bedbugsguide.com
(9) "How to Kill Bed Bugs in Carpet," whatdobedbugslook-like.net, Copyright 2013

In addition, whole house systems are disclosed which use heat as means of killing the pests. See "ThermaPure® Inc. Receives New U.S. Patent for the Use of Heat Technology to Kill Bed Bugs", see Hedman, U.S. Pat. No. 7,690,148, issued Apr. 6, 2010 and Hedman, US2011/0219665.

Various other patents and patent applications disclose methods for controlling bed bugs. These can be classified as either chemical, which include insecticides, formulations of insecticides, and repellants; or physical devices, which includes heat delivery systems, vacuum and steam cleaners and traps.

In the *Chemical and Engineering News* (Schulz, 2011 cited above) disclosure, the common insecticides in use against bed bugs are pyrethrins (pyrethrums). In addition, other compounds such as chorfenapyr and propoxur are insecticidally active against bedbugs. However, neither has been approved by the EPA for use in the home.

Other disclosures describe various other compounds and formulations of compounds. For example, US 2011/0213038 describes formulations containing at least one compound selected from carvone, linalool, styryl alcohol, dihydrocarbone, tetracyrocarvone and mixtures thereof. WO2010/115065 discloses microemulsion pesticide formulations using these and other compounds together with a fatty acid for enhanced pest control. US 2011/0256196 discloses boron-containing compounds used to control insects, formulated with surfactants. The surfactants disclosed are cationic, e.g., quaternary ammonium salts.

WO 2005/070210 discloses mixtures made up of a pyrethroid and another insecticide selected from imidacloprid, niathiazine, thamethoxam, dinotefuran, nitenpyram, thiaclo-prid, clothiandine and chlorfenapyr, and the use of such mixtures for controlling household insect pests, including bed bugs.

Impregnation of insecticides/repellents into carpet fibers is disclosed in US 2007/0196412 and U.S. Pat. No. 5,587,221 discloses carpet which has been pretreated with insecticidal compounds.

Monitoring and controlling bed bug infestation is also disclosed in US 2011/0289824, using a detection device that comprises an insect attractant, an arresting, and/or aggregating compound, which may also be combined with an insecticide or pheromone. US 2009/0145019 discloses a device which employs thermal, chemical and gaseous ($CO_2$) attractants in combination to attract, trap and optional kill bedbugs from any dwelling.

The use of simple devices that generate heat/steam to destroy or exterminate insects has been disclosed in U.S. Pat. No. 125,557 and U.S. Pat. No. 601,168.

A vacuum designed to collect and kill insects, specifically fleas, has been disclosed in US 2010/0205767.

Despite the numerous published methods, devices and compounds, there has been an increase pest infestation, and more effective, more economical, and safer methods to control arthropods, particularly bed bugs, in interior dwellings are needed.

SUMMARY OF THE INVENTION

While many individual methods to combat the problem of controlling arthropod infestations in interior dwelling have been tried, the disclosed methods or systems currently in use have not effectively solved the ongoing problem. In accordance with this invention, the problem is solved by using methods and compositions that provide more effective cleaning of surfaces and objects within the interior dwelling space and residual insect control. The method comprises the cleaning of surfaces and objects within an interior dwelling space using a high efficiency water extraction device, utilizing water that is heated to a temperature sufficient to kill or immobilize the pest, and to which is added a cleaning agent comprising a surfactant that imparts a surface tension of about 30 dynes/cm or lower, (a "super wetting agent"); in combination with application of an effective arthropod control composition to surfaces and objects within the interior dwelling spaces, the arthropod control composition comprising an arthropod control agent and a surfactant that imparts a surface tension of about 30 dynes/cm or lower. We have found that the addition of a the "super wetting agent" surfactant to cleaning and arthropod control agents, provides much enhanced ability over conventional surfactants to physically remove and kill arthropods in all life forms (adults, larvae and eggs), especially Bed Bugs (*C. Lectularius*), and more effectively inhibits the reoccurrence and spreading of the infestation in the dwelling space.

One embodiment of the invention comprises a method for removal of arthropod infestations from accessible surfaces and objects located in the interior dwelling space, wherein the surfaces and objects include floors, floor coverings, upholstery, and soft furnishings present within the interior dwelling space, by using a cleaning composition containing a super wetting agent.

A second embodiment further comprises a method for removal of arthropod infestations from accessible surfaces and objects by using an effective hot water extraction device, wherein the device is equipped with a high recovery application wand.

A third embodiment of the invention further comprises a method of controlling an arthropod infestation in an interior dwelling, by treatment of accessible surfaces and objects within the dwelling with an arthropod control composition, the composition comprising an arthropod control agent labeled for indoor use, and a super wetting agent.

A fourth embodiment of the invention is the method described hereinabove, wherein the super wetting agent is selected from siloxane surfactants and fluorochemical surfactants.

A fifth embodiment of the invention is the method described hereinabove, wherein the arthropod is bed bug (*C. lectularius*).

DETAILED DESCRIPTION OF THE INVENTION

In accordance with the invention, the method for control of arthropod pest infestation comprises the steps of cleaning the infested dwelling space and objects using a cleaning agent composition, and treating the cleaned area and objects with an arthropod control composition.

In accordance with the invention, the interior dwelling spaces that are effectively treated by the methods of the invention are those occupied by mammals, particularly humans. Such dwellings include those where humans live and work, and include homes, offices, warehouses, factories, storage areas, apartments, condominiums, living quarters on sea vessels, indoor public areas, commercial stores, retail spaces, and the like.

An aspect of the invention is a method of using a cleaning composition for the removal and control of insect infestations in a dwelling, the composition comprising a surfactant which is effective for cleaning of flooring surfaces, carpet, upholstery, and soft surfaces; and a super wetting agent.

In an embodiment of the invention, the cleaning step uses a hot water extraction cleaning device containing the cleaning composition for the removal of the arthropod infestation, wherein the device is fitted with a high-recovery wand, is capable of heating the water/cleaning composition to a temperature high enough to remove and destroy the arthropods in all life forms, and has a water lifting capacity sufficient to remove at least about 15% of the applied water cleaning composition.

These types of machines are designed so as to apply hot water, under pressure, directly to the carpet or fabric to be cleaned. The hot water is supplied from a tank which optimally contains an effective cleaning composition. In accordance with the invention, the hot water/cleaning composition mixture is heated by the machine to a temperature sufficient to kill or immobilize the arthropod pest. Simultaneously as the hot water/cleaning composition is applied to the surface, a vacuum port in close proximity to the water nozzle allows the water to be recaptured and filtered. This type of high-recovery system is preferred because the applied spray of hot water is localized to the area being treated, with minimal impact on surrounding areas. This localized action increases the efficiency and efficacy of cleaning and removal of the arthropods at the point of application of cleaner/hot water, and prevents the scattering of arthropods and debris that occurs with less efficient cleaners. In addition, a wand that moves across surface without needing to be lifted also increases the effective removal of arthropods and prevents scatter of the arthropods. A greater efficiency of the vacuum results in a greater volume of recovered water. Efficiency of the vacuum can be measured by water lift capacity. An example, of an efficient hot water extraction device is one with a water lift capability of at least about 220 inches.

The hot water extraction device is used for the cleaning of all floors, upholstery, and soft furnishings. Floors to be cleaned in this fashion may be of any type, including carpeted, wooden, linoleum, brick, concrete, stone, marble, ceramic tile, vinyl tile, laminated wood or synthetic laminates, and the like. An embodiment of this device is one in which the water containing the cleaning composition and super wetting agent is heated by the machine and maintained in the machine's storage tank at temperature of at least about 120° F. The cleaning composition is applied under pressure to the surface to be cleaned, and immediately vacuumed back into the device tank. The device is preferably fitted with a high recovery wand, e.g., one fitted with an air induction cleaning head that removes at least about 15% of the applied water without spreading or splashing to neighboring surfaces. This type of action for such a device has been referred to as a "rolling water" action. In one embodiment of the invention, the hot water extraction device is a Powr-flite® model PFX1385, "Black Max Hot Water Carpet Extractor with Perfect Heat®" fitted with the Wonder Wand® attachment, with a water lift capacity of 220 inches (Tacony Inc., Ft. Worth, Tex.). A smaller 3 inch size Wonder Wand® tool can be used for similar cleaning of upholstery and curtains.

In accordance with the invention, the hot water extraction device using high pressure application of water is carried out using a cleaning composition comprising one or more super wetting agent surfactants. This super wetting agent may be pre-formulated with other components of the cleaning agent to be used. Super wetting agents include fluorochemical surfactants such as ZONYL® CAPSTONE® (Registered trademark of DuPont), NOVEC™ (Trademark of 3M Company), and LODYNE™ (Trademark of Ciba Specialty Chemicals Corporation), and/or siloxane surfactants such as XIAMETER® (registered trademark of Dow Corning Corporation), MASIL® (registered trademark of Lubrizol Corporation), and RHODORSIL® (registered trademark of Rhodia Chimie Corporation). The addition of the super wetting agent surfactant lowers the surface tension of the cleaning composition to a value in the range from about 15 dynes/cm to 30 dynes/cm.

In addition to super wetting agents, other components typically present in a cleaning agent composition include builders, pH adjusters, hard water sequestering agents, anti-soiling agents, and other surfactants.

The choice of the super wetting agent to be included in the cleaning agent composition will depend upon the nature of the other surfactants in the cleaning solution. For example, a carpet cleaning agent that contains anionic surfactants will require the use of a non-ionic or an anionic super wetting agent.

In accordance with the invention, the carpet, upholstery, and soft furnishings may be comprised of natural materials such as, but not limited to wool, leather, cotton, and jute; or synthetic materials such as nylon, polyester, and polypropylene; or blends of materials both natural and synthetic.

In accordance with the invention there is also provided a method of using arthropod control compositions for the control of arthropod infestations, said compositions comprising an arthropod control agent and a super wetting agent; wherein the super wetting agent is a siloxane surfactant or a fluorochemical surfactant.

An additional embodiment of the invention further comprises the treatment of foundation bedding, e.g., box springs and mattresses, with the arthropod control composition containing the super wetting agent, covering the treated bedding with an impermeable wrap, and allowing the wrap to remain in place for a period of time sufficient to kill any arthropod s which may exist within said bedding.

In accordance with one aspect of the invention, the arthropod infestation is due to one or more arthropod pests that are found in interior dwellings occupied by mammals, wherein the arthropod pests are selected from bed bug (*Cimex Lectularius*), flea, tick, mosquito, centipede, millipede, silverfish, cockroach, dust mite, and lice.

To enhance the effectiveness of the embodiments of the invention, prior cleaning of the interior dwelling space by convention means can also be carried out. This conventional cleaning includes floor cleaning, e.g., sweeping, vacuuming, and the like; and removal and cleaning/laundering of loose items such a small furniture, clothing, blankets, sheets, pillows and the like. Conventional cleaning methods include conventional vacuuming, e.g., with a commercial grade vacuum cleaner; wiping of all surfaces, including non-carpeted floors such as ceramic tile, marble, wood, wood laminate, synthetic laminate, linoleum, linoleum tile, vinyl tile, concrete, and brick; as well as baseboards, and countertops; removal of loose debris and refuse, cleaning and laundering of clothing and other washable fabrics such as draperies, curtains and the like. Small items which cannot be laundered by conventional means may be treated with heat, e.g., placed in a clothes dryer at high temperature of at least about 110° F. for about 10 minutes.

In another embodiment, the effective arthropodicide is chosen from the group consisting of pyrethrins, pyrethroids, propoxofur, carboxanilides, carbamates, imidacloprid, niathiazine, thamethoxam, dinotefuran, nitenpyram, thiacloprid, clothiandine and chlorfenapyr. The choice of arthropodicide is based on several factors, including the target arthropod to be controlled, the location of the infestation and the lack of undesirable properties such as human toxicity, odor, discoloring residue, speed of control ("knockdown") and long term effectiveness (persistence). A preferred arthropodicide is one that is registered and permissible by regulating authorities for use in the area to be treated, e.g., pyrethrins in the home. The effective arthropodicide is mixed with 0.001% to 10% super wetting agent containing a fluorochemical surfactant and/or siloxane surfactant. The addition of the super wetting agent results in more thorough coverage of the arthropod control agent throughout the infested dwelling space, and better wetting of all hydrophobic surfaces, including the exterior of eggs, larvae, and adult exoskeletons, thus allowing increased transport of pesticide to the target and better residual control.

Another aspect of the invention is the treatment of bedding. Because arthropods such as bed bugs and their eggs and larvae are tenaciously attached to bedding and may hide inside cracks and crevices or within the bedding itself, the method involves the treatment of such bedding first with the arthropod control compositions described hereinabove, followed by a complete covering with an impermeable material. Examples of such coverings are zippered covers manufactured using clear vinyl, unbleached cotton or microfiber polyester, available, for example from Shop Bedding.com, Brooklyn, N.Y.

In an embodiment of the invention, the impermeable wrap used to cover bedding, preferably all mattresses and box springs, is selected from a fabric or material that prohibits any arthropod that may be deep inside the bedding from escaping, thereby causing eventual death of the arthropod. Preferable wrap material also seals in any applied arthropodicide, further contributing to the death of any arthropods within. Suitable fabrics or material include microfiber polyester, vinyl and the like.

In yet another embodiment, the impermeable wrap is allowed to remain in place for period of time sufficient to result in pest death, preferably at least about 30 days or more.

Another embodiment of the invention is a process for effectively controlling bed bugs comprising the use of an effective cleaning compositions, cleaning devices, arthropod control compositions and physical bathers. The process is useful for controlling beg bugs in dwellings where humans reside, including but not limited to houses, apartments, condominiums, offices, warehouses, factories, and the like. A particular object of this invention is to provide a method for effectively controlling bed bugs which may infest areas where humans sleep. The bed bug may or may not be visible during the day or waking hours, but emerge from nesting places at night when humans are asleep, to feed on human blood.

In contrast to the disclosed methods for controlling bed bugs, such as chemical treatment alone and heating systems, the present method uses conventional and readily available arthropodicides, preferably pyrethrins or pyrethrin-containing formulations such as RIPTIDE®, or PRENTOX®, in conjunction with cleaning methods and equipment that are particularly suitable for entrapping and removing bed bugs, their larvae and eggs from carpet and fabrics, as well measures that control and prevent re-infestation of beg bugs from deep within bedding by using a combination of arthropodicides and physical barriers. Together the overall method and procedure assures more complete removal and control of not only active bed bugs, but also dormant larvae and eggs from most surfaces and bedding.

Bed bugs, their larvae and eggs are often found to adhere strongly to fabrics and are not easily removed by simple mechanical means. The egg masses in particular are attached to fabric with a strongly adhesive hydrophobic substance, making removing difficult. Thus the use of a cleaning agent that contains a super wetting agent enhances the penetration of the cleaning agent into the fabric and to attached egg masses and larvae, facilitating their removal by the high efficiency water extraction device.

It is to be understood that in carrying out the methods of this invention, operators of the hot water extraction device and applicators of arthropod control compositions will use discretion and judgment in the use of cleaning solutions and arthropodicide treatment. Although the more thoroughly that the method of the invention is carried out, it is to be understood that from a practical perspective, it is not always possible to clean every surface or apply arthropodicide to each and every area of the dwelling space that is in need of treatment. Those who are trained in either carpet cleaning or extermination techniques will understand that each space will be assessed and inspected in order to adjust the methods as appropriate for each dwelling space. While it is advisable that occupants of the dwelling space are absent during treatment, it is not absolutely necessary, provided safety precautions are taken to avoid exposure to arthropodicides. It is also to be understood that an inspection would normally be carried out at reasonable intervals to evaluate the effectiveness of the treatment methods and that a repetition of the method may be necessary in specific areas of the dwelling space that may still show signs of infestation.

Definitions

As used herein, the term "arthropod infestation" refers to the unwanted presence of undesirable arthropods, particularly insects and spiders, in an interior dwelling space. The level of infestation may vary from slight to severe as measured by such factors as the number individual arthropods (adults, larvae or eggs) observed per square foot, the frequency of bites to inhabitants, or the observance of other visible signs of infestation such as detritus, waste products, webs, egg casings and the like.

As used herein, the term "surfactant" is any of the surface active agents that may be used for the stated purpose. Surfactants may be anionic, cationic, amphoteric, zwitterionic, or non-ionic in chemical nature. The surfactants useful herein include anionic, nonionic, amphoteric, zwitterionic, or mixtures thereof including those with silicon or fluorine.

Examples of suitable anionic surfactants include alkali metal or ammonium salts of fatty acids; alcohol sulfates; alcohol sulfonates; alcohol phosphates; sodium dioctyl sulfosuccinate; alcohol phosphonates; $C_8$ to $C_{22}$ alkyl sulfonates; disodium lauric sulfosuccinates; disodium lauramido MEA sulfosuccinates; salts of $C_8$ to $C_{20}$ alkylbenzene sulfonates; $C_8$ to $C_{22}$ primary or secondary alkane sulfonates; $C_8$ to $C_{24}$ olefin sulfonates; sulfonated polycarboxylic acids prepared by sulfonation of pyrolyzed product of alkaline earth metal citrates; $C_8$ to $C_{24}$ alkylpolyglycolether sulfonates containing up to 10 mols of ethylene oxide, and the like. Suitable salts herein refer particularly to sodium, potassium, ammonium, and substituted ammonium salts such as mono-, di-, and triethanolamine salts. Anionic surfactants are described in "Surface Active Agents and Detergents" Vol. I and II) by Schwartz, Perry and Berch.

Examples of suitable nonionic synthetic detergents or surfactants useful herein include linear ethoxylated medium to long chain alcohols; propoxylated/ethoxylated medium to long chain alcohols; ethoxylated nonylphenols; ethoxylated octylphenols; ethoxylated primary alcohols; ethylene oxide/propylene oxide block copolymers; condensation products of ethylene oxide, propylene oxide and/or butylene oxide with $C_8$-$C_{18}$ alkylphenols; $C_8$-$C_{18}$ primary or secondary aliphatic alcohols; $C_8$-$C_{18}$ fatty acid amides; tertiary amine oxides with one $C_{\cdot 8}$-$C_{18}$ alkyl chain and two $C_1$-$C_3$ alkyl chains.

Suitable anionic and nonionic surfactants are discussed in U.S. Pat. No. 5,534,167 and in U.S. Pat. No. 5,004,557 herein incorporated by reference in their entirety.

Examples of amphoteric or zwitterionic detergents are N-alkylamino acids, sulphobetaines, and condensation products of fatty acids with protein hydrolysates. Amphoteric or zwitterionic surfactants are also discussed in U.S. Pat. No. 5,004,557 incorporated by reference above.

Mixtures of the various types of surfactants may also be used, and preference is given to mixtures of anionic and nonionic surfactants. Soaps, in the form of their sodium, potassium, and substituted ammonium salts such as of polymerized fatty acids, may also be used, preferably in conjunction with an anionic and/or a nonionic synthetic detergent.

The term "super wetting agents" refer to surfactants that produce a superficial (air-aqueous solution) tension below about 30 dynes/cm. Some super wetting agents are known that produce a surface tension as low as about 15 dynes/cm, which is about twice as low as the value reachable with a corresponding tension-reducing hydrocarbon surfactant. Examples of super wetting agents are fluorochemical surfactants and siloxane surfactants.

Siloxane surfactants are a special class of non-ionic surfactants and include XIAMETER® MEM-0949 EMULSION, XIAMETER® MEM-0939 EMULSION, XIAMETER® OFX-5103 FLUID, XIAMETER® OFX-0309 FLUID, XIAMETER® OFX-5211 SUPERWETTING AGENT. GRANSURF® and Dow Corning XIAMETER Q2-5211 super wetting agent [methyl(propylhydroxide, ethoxylated)bis(trimethylsiloxy)silane.]

Fluorochemical surfactants are another special class of surfactants in which a plurality of hydrogen atoms in a hydrocarbon surfactant is substituted by fluorine atoms to produce a hydrophobic region of the resulting surfactant molecule. Another region of the molecule is generally a hydrophilic moiety. For example, such hydrophilic moieties can be a carboxylic acid, a sulfate, or phosphate, providing anionic surfactants; or can be an amine or ammonium derivative, providing cationic surfactants. Zwitterionic surfactants exist if both an anionic and cationic moiety are present in the same surfactant molecule. Examples of fluorochemical surfactants product lines include CAPSTONE®, (formerly ZONYL®), NOVEC™, LODYNE™. FLEXIWET® NI-M, FLEXIWET® NI-M 100, FLEXIWET® SSE, and THETAWET™ FS-8000 (Trademarks of Innovative Chemical Technologies, Inc.)

As used herein, the terms "arthropod control agent", "arthropodicidal compound" or "arthropodicide" all refer to a substance which causes death to arthropod, particularly insects or arachnids (spiders), by any mode of action. Arthropod control agents include insecticides of various classes, for example, pyrethrins, pyrethroids, propoxofur, carboxanilides, carbamates, imidacloprid, niathiazine, thamethoxam, dinotefuran, nitenpyram, thiacloprid, clothiandine, chlorfenapyr and the like. An arthropod control agent and can applied as a single compound or in combination with another arthropod control agent in order to kill or control the target arthropod pest. The arthropod pest may be in the adult, nymph, larvae or egg form.

As used herein, the terms "pyrethrin" or "pyrethrums" refers to the class of compounds derived from perennial plant pyrethrum (*Chrysanthemum cinerariaefolium*) and currently in use for the control of arthropods.

As used herein, the term "carpet" refers to any fabric floor covering, whether wall-to-wall or area rugs. The fabric may be of any in common use such as nylon, wool, polyester and the like.

General Methods Used in the Invention

The hot water extraction cleaning device can be any of the commercially available devices used for cleaning carpet. A commercial grade cleaner is preferred, for example the Powr-Flite® Model Black Max Hot Water Carpet Extractor with Perfect Heat® (Tacony, Inc.).

The carpet cleaning wand used in conjunction with the hot water extraction clearing device is preferably one in which the liquid cleaning solution is applied to the carpet as a fine (atomized) high pressure spray, and in which there is a high recovery of liquid (e.g., 15% or more) by the vacuum back in the tank. The preferred cleaning wand is one that provides a controlled spray area, so as to prevent disturbing nearby untreated areas and dispersing arthropods, arthropod eggs or larvae. An example of such a wand is the Wonderwand® by Powr-Flite® (Tacony Inc.)

Descriptions of suitable wands include but are not limited to that in US 2006/0248677, U.S. Pat. No. 6,055,699, U.S. Pat. No. 5,555,598, U.S. Pat. No. 6,263,39 and U.S. Pat. No. 7,617,564, all of which are incorporated herein by reference.

Liquid cleaning agents incorporating surfactants are known. For example U.S. Pat. No. 5,338,475 (Corey et al.) discloses a carpet cleaning composition including hydrogen peroxide and an nonionic, anionic or amphoteric surfactant from about 0.05-5%, by weight, advising the selection of the selection of a surfactant that when employed in the recommended concentrations does not leave a tacky or oily residue. U.S. Pat. No. 4,490,270 (Hackett, et al.) is directed to a sanitizing liquid shampoo for carpets, including 0.1-20% surfactant, by weight. Suggested surfactants include sodium lauryl sulfate and sodium lauryl ether sulfate. U.S. Pat. No. 5,384,597 (Rees) teaches stable aqueous soft surface cleaning compositions containing a peroxygen reagent and an anionic surfactants such a sodium lauryl sulfate which can concentrate 0.4 to 0.6 percent of a base composition. U.S. Pat. No. 5,492,540 (Leifheit, et al.) discloses a soft surface cleaning composition including from about 0.2% to about 6.0% of a surfactant by weight. Leifheit teaches using surfactants for which the final composition dries to a non-tacky or non-sticky residue, to reduce the likelihood of resoiling fibers after their initial cleaning.

To any of the widely used cleaning agents, such as those described above, is added a super wetting agent, i.e., an agent that reduces the surface tension of the cleaning agent mixture to a range of from about 15 to about 30 dynes/cm. Cleaning agents that are pre-formulated with a super wetting agent are also effective materials for use on the appropriate fabric, for example, DuPont CAPSTONE® CPS, as well as other CAPSTONE® surfactants for use on carpet.

Examples of effective cleaning agent/super wetting agent compositions in accordance with the invention are shown in Table 1 hereinbelow.

TABLE 1

Cleaning Agent-Super Wetting Agent Compositions

| Entry No. | Cleaning Agent | Super Wetting Agent Additive | Amount of Super Wetting Agent Added (wt/wt) |
|---|---|---|---|
| 1 | CAPSTONE CPS | 0 | 0 |
| 2 | FLEXICLEAN cc-307 | 0 | 0 |
| 3 | FLEXICLEAN RTD-3 | 0 | 0 |
| 4 | FLEXISPERSE | 0 | 0 |
| 5 | FLEXIWET NF | 0 | 0 |
| 6 | MATRIX CONFIDENCE Premium Extractor Detergent[1] | CAPSTONE ® FS-31[2] | 0.01-2% |
| 7 | MATRIX CONFIDENCE Premium Extractor Detergent | CAPSTONE ® FS-3100 | 0.01-2% |
| 8 | MATRIX CONFIDENCE Premium Extractor Detergent | CAPSTONE ® - 34 | 0.01-2% |
| 9 | MATRIX CONFIDENCE Premium Extractor Detergent | CAPSTONE ® - 35 | 0.01-2% |
| 10 | MATRIX CONFIDENCE Premium Extractor Detergent | NOVEC ® - FC-4430[3] | 0.01-2% |
| 11 | MATRIX CONFIDENCE Premium Extractor Detergent | NOVEC ® FC-4432 | 0.01-2% |
| 12 | MATRIX CONFIDENCE Premium Extractor Detergent | NOVEC ® FC-4433 | 0.01-2% |
| 13 | MATRIX CONFIDENCE Premium Extractor Detergent | FLEXIWET ® NI-M[4] | 0.01-2% |
| 14 | MATRIX CONFIDENCE Premium Extractor Detergent | FLEXIWET ® NI-M100 | 0.01-2% |
| 15 | MATRIX CONFIDENCE Premium Extractor Detergent | FLEXIPEL ® S-11WS | 0.01-2% |

TABLE 1-continued

Cleaning Agent-Super Wetting Agent Compositions

| Entry No. | Cleaning Agent | Super Wetting Agent Additive | Amount of Super Wetting Agent Added (wt/wt) |
|---|---|---|---|
| 16 | MATRIX CONFIDENCE Premium Extractor Detergent | FLEXIWET ® SSE | 0.01-2% |
| 17 | MATRIX CONFIDENCE Premium Extractor Detergent | THETAWET ® FS-8000 | 0.01-2% |
| 18 | MATRIX CONFIDENCE Premium Extractor Detergent | THETAWET ® FS-8050 | 0.01-2% |
| 19 | MATRIX CONFIDENCE Premium Extractor Detergent | THETAWET ® FS-8100 | 0.01-2% |
| 20 | MATRIX CONFIDENCE Premium Extractor Detergent | THETAWET ® FS-8150 | 0.01-2% |
| 21 | MASTER CLEAN ™ - premium liquid detergent[5] | CAPSTONE ® FS-31 | 0.01-2% |
| 22 | MASTER CLEAN ™ - premium liquid detergent | CAPSTONE ® FS-3100 | 0.01-2% |
| 23 | MASTER CLEAN ™ - premium liquid detergent | CAPSTONE ® - 34 | 0.01-2% |
| 24 | MASTER CLEAN ™ - premium liquid detergent | CAPSTONE ® - 35 | 0.01-2% |
| 25 | MASTER CLEAN ™ - premium liquid detergent | NOVEC ® - FC-4430 | 0.01-2% |
| 26 | MASTER CLEAN ™ - premium liquid detergent | NOVEC ® FC-4432 | 0.01-2% |
| 27 | MASTER CLEAN ™ - premium liquid detergent | NOVEC ® FC-4433 | 0.01-2% |
| 28 | MASTER CLEAN ™ - premium liquid detergent | FLEXIWET ® NI-M | 0.01-2% |
| 29 | MASTER CLEAN ™ - premium liquid detergent | FLEXIWET ® NI-M100 | 0.01-2% |
| 30 | MASTER CLEAN ™ - premium liquid detergent | FLEXIPEL ® S-11WS | 0.01-2% |
| 31 | MASTER CLEAN ™ - premium liquid detergent | FLEXIWET ® SSE | 0.01-2% |
| 32 | MASTER CLEAN ™ - premium liquid detergent | THETAWET ® FS-8000 | 0.01-2% |
| 33 | MASTER CLEAN ™ - premium liquid detergent | THETAWET ® FS-8050 | 0.01-2% |
| 34 | MASTER CLEAN ™ - premium liquid detergent | THETAWET ® FS-8100 | 0.01-2% |
| 35 | MASTER CLEAN ™ - premium liquid detergent | THETAWET ® FS-8150 | 0.01-2% |
| 36 | MASTER CLEAN ™ - premium powder detergent | CAPSTONE ® FS-31 | 0.01-2% |
| 37 | MASTER CLEAN ™ - premium powder detergent | CAPSTONE ® FS-3100 | 0.01-2% |
| 38 | MASTER CLEAN ™ - premium powder detergent | CAPSTONE ® - 34 | 0.01-2% |
| 39 | MASTER CLEAN ™ - premium powder detergent | CAPSTONE ® - 35 | 0.01-2% |
| 40 | MASTER CLEAN ™ - premium powder detergent | NOVEC ® - FC-4430 | 0.01-2% |
| 41 | MASTER CLEAN ™ - premium powder detergent | NOVEC ® FC-4432 | 0.01-2% |
| 42 | MASTER CLEAN ™ - premium powder detergent | NOVEC ® FC-4433 | 0.01-2% |
| 43 | MASTER CLEAN ™ - premium powder detergent | FLEXIWET ® NI-M | 0.01-2% |
| 44 | MASTER CLEAN ™ - premium powder detergent | FLEXIWET ® NI-M100 | 0.01-2% |
| 45 | MASTER CLEAN ™ - premium powder detergent | FLEXIPEL ® S-11WS | 0.01-2% |
| 46 | MASTER CLEAN ™ - premium powder detergent | FLEXIWET ® SSE | 0.01-2% |
| 47 | MASTER CLEAN ™ - premium powder detergent | THETAWET ® FS-8000 | 0.01-2% |
| 48 | MASTER CLEAN ™ - premium powder detergent | THETAWET ® FS-8050 | 0.01-2% |
| 49 | MASTER CLEAN ™ - premium powder detergent | THETAWET ® FS-8100 | 0.01-2% |
| 50 | MASTER CLEAN ™ - premium powder detergent | THETAWET ® FS-8150 | 0.01-2% |
| 51 | ONE STEP ™ Liquid - All fiber detergent[6] | CAPSTONE ® - 34 | 0.01-2% |
| 52 | ONE STEP ™ Liquid - All fiber detergent | CAPSTONE ® - 35 | 0.01-2% |
| 53 | ONE STEP ™ Liquid - All fiber detergent | NOVEC ® - FC-4430 | 0.01-2% |
| 54 | ONE STEP ™ Liquid - All fiber detergent | NOVEC ® FC-4432 | 0.01-2% |
| 55 | ONE STEP ™ Liquid - All fiber detergent | NOVEC ® FC-4433 | 0.01-2% |
| 56 | ONE STEP ™ Liquid - All fiber detergent | FLEXIWET ® NI-M | 0.01-2% |
| 57 | ONE STEP ™ Liquid - All fiber detergent | FLEXIWET ® NI-M100 | 0.01-2% |
| 58 | ONE STEP ™ Liquid - All fiber detergent | FLEXIPEL ® S-11WS | 0.01-2% |
| 59 | ONE STEP ™ Liquid - All fiber detergent | FLEXIWET ® SSE | 0.01-2% |
| 60 | ONE STEP ™ Liquid - All fiber detergent | THETAWET ® FS-8000 | 0.01-2% |
| 61 | ONE STEP ™ Liquid - All fiber detergent | THETAWET ® FS-8050 | 0.01-2% |
| 62 | ONE STEP ™ Liquid - All fiber detergent | THETAWET ® FS-8100 | 0.01-2% |
| 63 | ONE STEP ™ Liquid - All fiber detergent | THETAWET ® FS-8150 | 0.01-2% |
| 64 | HYDRA-CLEAN[7] | CAPSTONE ® FS-31 | 0.01-2% |
| 65 | HYDRA-CLEAN | CAPSTONE ® FS-3100 | 0.01-2% |
| 66 | HYDRA-CLEAN | CAPSTONE ® - 34 | 0.01-2% |
| 67 | HYDRA-CLEAN | CAPSTONE ® - 35 | 0.01-2% |
| 68 | HYDRA-CLEAN | NOVEC ® - FC-4430 | 0.01-2% |
| 69 | HYDRA-CLEAN | NOVEC ® FC-4432 | 0.01-2% |
| 70 | HYDRA-CLEAN | NOVEC ® FC-4433 | 0.01-2% |

TABLE 1-continued

Cleaning Agent-Super Wetting Agent Compositions

| Entry No. | Cleaning Agent | Super Wetting Agent Additive | Amount of Super Wetting Agent Added (wt/wt) |
|---|---|---|---|
| 7 | HYDRA-CLEAN | FLEXIWET ® NI-M | 0.01-2% |
| 72 | HYDRA-CLEAN | FLEXIWET ® NI-M100 | 0.01-2% |
| 73 | HYDRA-CLEAN | FLEXIPEL ® S-11WS | 0.01-2% |
| 74 | HYDRA-CLEAN | FLEXIWET ® SSE | 0.01-2% |
| 75 | HYDRA-CLEAN | THETAWET ® FS-8000 | 0.01-2% |
| 76 | HYDRA-CLEAN | THETAWET ® FS-8050 | 0.01-2% |
| 77 | HYDRA-CLEAN | THETAWET ® FS-8100 | 0.01-2% |
| 78 | HYDRA-CLEAN | THETAWET ® FS-8150 | 0.01-2% |
| 79 | HYDRA-DRI[8] | CAPSTONE ® FS-31 | 0.01-2% |
| 80 | TOUGH GUY Low - Foam Extraction Cleaner[9] | CAPSTONE ® FS-3100 | 0.01-2% |
| 81 | TOUGH GUY Low - Foam Extraction Cleaner | CAPSTONE ® - 34 | 0.01-2% |
| 82 | TOUGH GUY Low - Foam Extraction Cleaner | CAPSTONE ® - 35 | 0.01-2% |
| 83 | TOUGH GUY Low - Foam Extraction Cleaner | NOVEC ® - FC-4430 | 0.01-2% |
| 84 | TOUGH GUY Low - Foam Extraction Cleaner | NOVEC ® FC-4432 | 0.01-2% |
| 85 | TOUGH GUY Low - Foam Extraction Cleaner | NOVEC ® FC-4433 | 0.01-2% |
| 86 | TOUGH GUY Low - Foam Extraction Cleaner | FLEXIWET ® NI-M | 0.01-2% |
| 87 | TOUGH GUY Low - Foam Extraction Cleaner | FLEXIWET ® NI-M100 | 0.01-2% |
| 88 | TOUGH GUY Low - Foam Extraction Cleaner | FLEXIPEL ® S-11WS | 0.01-2% |
| 89 | TOUGH GUY Low - Foam Extraction Cleaner | FLEXIWET ® SSE | 0.01-2% |
| 90 | TOUGH GUY Low - Foam Extraction Cleaner | THETAWET ® FS-8000 | 0.01-2% |
| 91 | TOUGH GUY Low - Foam Extraction Cleaner | THETAWET ® FS-8050 | 0.01-2% |
| 92 | TOUGH GUY Low - Foam Extraction Cleaner | THETAWET ® FS-8100 | 0.01-2% |
| 93 | TOUGH GUY Low - Foam Extraction Cleaner | THETAWET ® FS-8150 | 0.01-2% |

[1]MATRIX CONFIDENCE is a brand of Jon Don
[2]CAPSTONE ® is a registered trademark of E. I. du Pont de Nemours and Company
[3]NOVEC ® is a registered trademark of the 3M corporation
[4]FLEXIWET ®, THETAWET ®, and FLEXIPEL ® are registered trademarks of Innovative Chemical Technologies, Inc., 103 Walnut Grove Rd, Cartersville, GA 30120
[5]MASTER CLEAN is a trademark of Master Blend Corporation
[6]ONE STEP is a trademark of Master Blend Corporation
[7]HYDRA-CLEAN is a brand of Hydramaster
[8]HYDRA-DRI is a brand of Hydramaster
[9]TOUGH GUY is a brand of Grainger Corporation The arthropod control agents used are obtained from normal commercial sources, and include pyrethrin products such as RIPTIDE®, (Registered Trademark of McLaughlin Gormley King Company) and PRENTOX® (Registered Trademark of Prentiss Incorporated). The commercial formulations of these compounds may contain additional components such as synergists (e.g., piperonyl butoxide, butylcarbityl) (6-propylpiperonyl)ether) and emulsifiers (e.g., glycol ethers).

Application of the arthropod control agents to which a super wetting agent is added (the arthropod control composition) can be accomplished using standard spraying application systems such as a hand-held sprayer, or other standard methods of application used in the home for treatment of arthropod infestations. Treatment is applied to floors, baseboards and other accessible spaces, cracks and crevices between walls and floors, furniture, countertop surfaces, areas under furniture (particularly beds), heating and cooling vents and registers, window sills, door thresholds, and any other points where arthropods may gain entry into a dwelling. As much of the dwelling is treated as possible, including all living areas, closets other storage areas.

Portable objects and furnishings that are removed can be cleaned using the hot water extraction device fitted with the appropriate wand attachment, or where feasible, individually laundered, and then they can also be treated with the arthropod control composition. Small items can also be treated with heat, e.g., by placement in a hot air dryer at about 110° F., even if laundering is impractical. They can also similarly be treated with the arthropod control composition.

The use of arthropod control agents is conducted in accordance with the requirements listed on the label of the compounds selected.

EXAMPLES

Embodiments of the present invention will now be described by way of example only with respect to the following examples.

General Procedures

Example 1. Preparatory Vacuum Cleaning

The insect infested area is prepared by vacuum cleaning, preferably with a commercial-grade vacuum cleaner fitted with a disposable bag which collects dust, insect and small debris. All accessible floors (both hard surface and carpet) are vacuumed thoroughly. The vacuum may be a sweeper type unit, or a wand with or without powered brushes. Surfaces of all furniture (e.g., sofas, armchairs, etc.) mattresses and box springs are then vacuumed using a conventional vacuum cleaner attachment. Before powering off the vacuum cleaner motor, a household insecticide (e.g., Raid® Bed Bug and Flea Killer, a Registered Trademark of S.C. Johnson, 3 N-octyl bicycloheptene dicarboximide, is sprayed into the opening while running.

Example 2. Hot Water Extraction Cleaning

A solution of DuPont CAPSTONE® CPS (manufactured by E. I. du Pont de Nemours and Company, Wilmington, Del. USA) (8 oz. per 1 gal water) (formerly ZONYL® 8929B) is prepared and added to the tank of a Powr-Flite® model Black Max Hot Water Carpet Extractor with Perfect Heat® commercial grade hot water extractor. Carpet is cleaned using a Powr-Flite® Wonder Wand cleaning wand. Spent water is discarded. Fabric on all furniture (sofas, armchairs, etc.) is cleaned with a hand tool designed for use with the hot water extractor.

Example 3. Formulations for Control of *C. Lectularius*

Preparation of a PRENTOX® Emulsifiable Spray

In a 2 gal sprayer, is placed 1 gal of PRENTOX® (PRENTOX® 303 EMUSIFIABLE CONCENTRATE, 3% pyrethrins and 30% piperonyl butoxide) and water is added to the 2 gallon mark. To this is added 20 mL of "AB-1 Inert" a super wetting agent XIAMETER® OFX-5211 (formerly Dow Corning Q2-5211). The container is closed and shaken for 30 sec.

Preparation of RIPTIDE® Spray Mixture

In a 2 gal sprayer is placed 26 oz. (3¼ cups or 770 mL) of RIPTIDE® (5% Pyrethrins, 25% Piperonyl butoxide, Technical) and water is added to the 2 gal mark. To this mixture is added 20 (30) mL of "AB-1 Inert" XIAMETER® OFX-5211 (formerly Dow Corning Q2-5211 super wetting agent. (Methyl(propylhydroxide, ethoxylated)bis(trimethylsiloxy)silane). The container is closed and shaken for 30 sec. The mixtures can be stored overnight and used with in a 24 h period, agitating prior to each use.

The method described in Example 3 above is used for the preparation of other arthropod control formulations, by substituting XIAMETER® OFX-5211 with one of the super wetting agents listed in Table 2 below.

TABLE 2

Examples of Surfactant additives

| Entry Number | Surfactant Additive | Range (wt/wt) |
|---|---|---|
| 1 | GRANSURF ® 50C-HM[1] | 0.001-2% |
| 2 | THOROUGHBRED ®[2] | 0.001-2% |
| 3 | XIAMETER ® OFX-0077 FLUID[3] | 0.001-2% |
| 4 | XIAMETER ® OFX-0309 FLUID | 0.001-2% |
| 5 | XIAMETER ® OFX-5211 | 0.001-2% |
| | SUPERWETTING AGENT | |
| 6 | CAPSTONE ® FS-31[4] | 0.001-2% |
| 7 | CAPSTONE ® FS-3100 | 0.001-2% |
| 8 | CAPSTONE ® - 34 | 0.001-2% |
| 9 | CAPSTONE ® - 35 | 0.001-2% |
| 10 | NOVEC ® - FC-4430[5] | 0.001-2% |
| 11 | NOVEC ® FC-4432 | 0.001-2% |
| 12 | NOVEC ® FC-4433 | 0.001-2% |
| 13 | FLEXIWET ® NI-M[6] | 0.001-2% |
| 14 | FLEXIWET ® NI-M100 | 0.001-2% |
| 15 | FLEXIPEL ® S-11WS[6] | 0.001-2% |
| 16 | FLEXIWET ® SSE | 0.001-2% |
| 17 | THETAWET ® FS-8000[6] | 0.001-2% |
| 18 | THETAWET ® FS-8050 | 0.001-2% |
| 19 | THETAWET ® FS-8100 | 0.001-2% |
| 20 | THETAWET ® FS-8150 | 0.001-2% |

[1]GRANSURF ® is a registered trademark of Grant Industries Inc., 125 Main Avenue, Elmwood Park, New Jersey 07407 USA
[2]THOROUGHBRED ® is a registered trademark of WINFIELD SOLUTIONS, LLC, P. O. Box 64589, St. Paul, MN 55164-0589
[3]XIAMETER ® is a registered trademark of Dow Corning
[4]CAPSTONE ® is a registered trademark of E. I. du Pont de Nemours and Company
[5]NOVEC ® is a registered trademark of the 3M corporation
[6]FLEXIWET ®, THETAWET ®, and FLEXIPEL ® are registered trademarks of Innovative Chemical Technologies, Inc., 103 Walnut Grove Rd, Cartersville, GA 30120

In addition, blends of two super wetting agents can be used for the preparation of arthropod control formulations, by substituting Dow Corning XIAMETER® OFX-5211 with one of the super wetting agent blends listed in Table 3 below. The blends are prepared by mixing the surfactants on a wt/wt ratio and then adding the appropriate amount to arthropod control agent.

TABLE 3

Super Wetting Agent Blends

| Entry No. | Surfactant A | Surfactant A percentage in surfactant blend | Surfactant B | Surfactant B percentage in surfactant blend | Percent of surfactant blend in final product (wt/wt) |
|---|---|---|---|---|---|
| 21 | XIAMETER ® OFX-0077 FLUID | 1-99% | CAPSTONE ® FS-31 | 1-99% | 0.001-2% |
| 22 | XIAMETER ® OFX-0077 FLUID | 1-99% | CAPSTONE ® FS-3100 | 1-99% | 0.001-2% |
| 23 | XIAMETER ® OFX-0077 FLUID | 1-99% | CAPSTONE ® - 34 | 1-99% | 0.001-2% |
| 24 | XIAMETER ® OFX-0077 FLUID | 1-99% | CAPSTONE ® - 35 | 1-99% | 0.001-2% |
| 25 | XIAMETER ® OFX-0077 FLUID | 1-99% | NOVEC ® - FC-4430 | 1-99% | 0.001-2% |
| 26 | XIAMETER ® OFX-0077 FLUID | 1-99% | NOVEC ® FC-4432 | 1-99% | 0.001-2% |
| 27 | XIAMETER ® OFX-0077 FLUID | 1-99% | NOVEC ® FC-4433 | 1-99% | 0.001-2% |
| 28 | XIAMETER ® OFX-0077 FLUID | 1-99% | FLEXIWET ® NI-M | 1-99% | 0.001-2% |
| 29 | XIAMETER ® OFX-0077 FLUID | 1-99% | FLEXIWET ® NI-M100 | 1-99% | 0.001-2% |
| 30 | XIAMETER ® OFX-0077 FLUID | 1-99% | FLEXIPEL ® S-11WS | 1-99% | 0.001-2% |
| 31 | XIAMETER ® OFX-0077 FLUID | 1-99% | FLEXIWET ® SSE | 1-99% | 0.001-2% |
| 32 | XIAMETER ® OFX-0077 FLUID | 1-99% | THETAWET ® FS-8000 | 1-99% | 0.001-2% |
| 33 | XIAMETER ® OFX-0077 FLUID | 1-99% | THETAWET ® FS-8050 | 1-99% | 0.001-2% |
| 34 | XIAMETER ® OFX-0077 FLUID | 1-99% | THETAWET ® FS-8100 | 1-99% | 0.001-2% |
| 35 | XIAMETER ® OFX-0077 FLUID | 1-99% | THETAWET ® FS-8150 | 1-99% | 0.001-2% |

TABLE 3-continued

Super Wetting Agent Blends

| Entry No. | Surfactant A | Surfactant A percentage in surfactant blend | Surfactant B | Surfactant B percentage in surfactant blend | Percent of surfactant blend in final product (wt/wt) |
|---|---|---|---|---|---|
| 36 | XIAMETER ® OFX-5211 SUPERWETTING AGENT | 1-99% | CAPSTONE ® FS-31 | 1-99% | 0.001-2% |
| 37 | XIAMETER ® OFX-5211 SUPERWETTING AGENT | 1-99% | CAPSTONE ® FS-3100 | 1-99% | 0.001-2% |
| 38 | XIAMETER ® OFX-5211 SUPERWETTING AGENT | 1-99% | CAPSTONE ® - 34 | 1-99% | 0.001-2% |
| 39 | XIAMETER ® OFX-5211 SUPERWETTING AGENT | 1-99% | CAPSTONE ® - 35 | 1-99% | 0.001-2% |
| 40 | XIAMETER ® OFX-5211 SUPERWETTING AGENT | 1-99% | NOVEC ® - FC-4430 | 1-99% | 0.001-2% |
| 41 | XIAMETER ® OFX-5211 SUPERWETTING AGENT | 1-99% | NOVEC ® FC-4432 | 1-99% | 0.001-2% |
| 42 | XIAMETER ® OFX-5211 SUPERWETTING AGENT | 1-99% | NOVEC ® FC-4433 | 1-99% | 0.001-2% |
| 43 | XIAMETER ® OFX-0309 FLUID | 1-99% | CAPSTONE ® FS-31 | 1-99% | 0.001-2% |
| 44 | XIAMETER ® OFX-0309 FLUID | 1-99% | FLEXIWET ® NI-M | 1-99% | 0.001-2% |
| 45 | XIAMETER ® OFX-0309 FLUID | 1-99% | FLEXIWET ® NI-M100 | 1-99% | 0.001-2% |
| 46 | XIAMETER ® OFX-0309 FLUID | 1-99% | FLEXIPEL ® S-11WS | 1-99% | 0.001-2% |
| 47 | XIAMETER ® OFX-0309 FLUID | 1-99% | FLEXIWET ® SSE | 1-99% | 0.001-2% |
| 48 | XIAMETER ® OFX-0309 FLUID | 1-99% | THETAWET ® FS-8000 | 1-99% | 0.001-2% |
| 49 | XIAMETER ® OFX-0309 FLUID | 1-99% | THETAWET FS-8050 | 1-99% | 0.001-2% |
| 50 | XIAMETER ® OFX-0309 FLUID | 1-99% | THETAWET FS-8100 | 1-99% | 0.001-2% |
| 51 | XIAMETER ® OFX-0309 FLUID | 1-99% | THETAWET FS-8150 | 1-99% | 0.001-2% |
| 52 | XIAMETER ® OFX-0309 FLUID | 1-99% | CAPSTONE ® FS-3100 | 1-99% | 0.001-2% |
| 53 | XIAMETER ® OFX-0309 FLUID | 1-99% | CAPSTONE ® - 34 | 1-99% | 0.001-2% |
| 54 | XIAMETER ® OFX-0309 FLUID | 1-99% | CAPSTONE ® - 35 | 1-99% | 0.001-2% |
| 55 | XIAMETER ® OFX-0309 FLUID | 1-99% | NOVEC ® - FC-4430 | 1-99% | 0.001-2% |
| 56 | XIAMETER ® OFX-0309 FLUID | 1-99% | NOVEC ® FC-4432 | 1-99% | 0.001-2% |
| 57 | XIAMETER ® OFX-0309 FLUID | 1-99% | NOVEC ® FC-4433 | 1-99% | 0.001-2% |
| 58 | XIAMETER ® OFX-0309 FLUID | 1-99% | FLEXIWET ® NI-M | 1-99% | 0.001-2% |
| 59 | XIAMETER ® OFX-0309 FLUID | 1-99% | FLEXIWET ® NI-M100 | 1-99% | 0.001-2% |
| 60 | XIAMETER ® OFX-0309 FLUID | 1-99% | FLEXIPEL ® S-11WS | 1-99% | 0.001-2% |
| 61 | XIAMETER ® OFX-0309 FLUID | 1-99% | FLEXIWET ® SSE | 1-99% | 0.001-2% |
| 62 | XIAMETER ® OFX-0309 FLUID | 1-99% | THETAWET ® FS-8000 | 1-99% | 0.001-2% |
| 63 | XIAMETER ® OFX-0309 FLUID | 1-99% | THETAWET FS-8050 | 1-99% | 0.001-2% |
| 64 | XIAMETER ® OFX-0309 FLUID | 1-99% | THETAWET FS-8100 | 1-99% | 0.001-2% |

TABLE 3-continued

Super Wetting Agent Blends

| Entry No. | Surfactant A | Surfactant A percentage in surfactant blend | Surfactant B | Surfactant B percentage in surfactant blend | Percent of surfactant blend in final product (wt/wt) |
|---|---|---|---|---|---|
| 65 | XIAMETER ® OFX-0309 FLUID | 1-99% | THETAWET FS-8150 | 1-99% | 0.001-2% |
| 66 | THOROUGHBRED ® | 1-99% | CAPSTONE ® FS-31 | 1-99% | 0.001-2% |
| 67 | THOROUGHBRED ® | 1-99% | CAPSTONE ® FS-3100 | 1-99% | 0.001-2% |
| 68 | THOROUGHBRED ® | 1-99% | CAPSTONE ® - 34 | 1-99% | 0.001-2% |
| 69 | THOROUGHBRED ® | 1-99% | CAPSTONE ® - 35 | 1-99% | 0.001-2% |
| 70 | THOROUGHBRED ® | 1-99% | NOVEC ® - FC-4430 | 1-99% | 0.001-2% |
| 71 | THOROUGHBRED ® | 1-99% | NOVEC ® FC-4432 | 1-99% | 0.001-2% |
| 72 | THOROUGHBRED ® | 1-99% | NOVEC ® FC-4433 | 1-99% | 0.001-2% |
| 73 | THOROUGHBRED ® | 1-99% | FLEXIWET ® NI-M | 1-99% | 0.001-2% |
| 74 | THOROUGHBRED ® | 1-99% | FLEXIWET ® NI-M100 | 1-99% | 0.001-2% |
| 75 | THOROUGHBRED ® | 1-99% | FLEXIPEL ® S-11WS | 1-99% | 0.001-2% |
| 76 | THOROUGHBRED ® | 1-99% | FLEXIWET ® SSE | 1-99% | 0.001-2% |
| 77 | THOROUGHBRED ® | 1-99% | THETAWET ® FS-8000 | 1-99% | 0.001-2% |
| 78 | THOROUGHBRED ® | 1-99% | THETAWET FS-8050 | 1-99% | 0.001-2% |
| 79 | THOROUGHBRED ® | 1-99% | THETAWET FS-8100 | 1-99% | 0.001-2% |
| 80 | THOROUGHBRED ® | 1-99% | THETAWET FS-8150 | 1-99% | 0.001-2% |
| 81 | GRANSURF ® 50C-HM | 1-99% | CAPSTONE ® FS-31 | 1-99% | 0.001-2% |
| 82 | GRANSURF ® 50C-HM | 1-99% | CAPSTONE ® FS-3100 | 1-99% | 0.001-2% |
| 83 | GRANSURF ® 50C-HM | 1-99% | CAPSTONE ® - 34 | 1-99% | 0.001-2% |
| 84 | GRANSURF ® 50C-HM | 1-99% | CAPSTONE ® - 35 | 1-99% | 0.001-2% |
| 85 | GRANSURF ® 50C-HM | 1-99% | NOVEC ® FC-4430 | 1-99% | 0.001-2% |
| 86 | GRANSURF ® 50C-HM | 1-99% | NOVEC ® FC-4432 | 1-99% | 0.001-2% |
| 87 | GRANSURF ® 50C-HM | 1-99% | NOVEC ® FC-4433 | 1-99% | 0.001-2% |
| 88 | GRANSURF ® 50C-HM | 1-99% | FLEXIWET ® NI-M | 1-99% | 0.001-2% |
| 89 | GRANSURF ® 50C-HM | 1-99% | FLEXIWET ® NI-M100 | 1-99% | 0.001-2% |
| 90 | GRANSURF ® 50C-HM | 1-99% | FLEXIPEL ® S-11WS | 1-99% | 0.001-2% |
| 91 | GRANSURF ® 50C-HM | 1-99% | FLEXIWET ® SSE | 1-99% | 0.001-2% |
| 92 | GRANSURF ® 50C-HM | 1-99% | THETAWET ® FS-8000 | 1-99% | 0.001-2% |
| 93 | GRANSURF ® 50C-HM | 1-99% | THETAWET ® FS-8050 | 1-99% | 0.001-2% |
| 94 | GRANSURF ® 50C-HM | 1-99% | THETAWET ® FS-8100 | 1-99% | 0.001-2% |
| 95 | GRANSURF ® 50C-HM | 1-99% | THETAWET ® FS-8150 | 1-99% | 0.001-2% |

Example 4. Treatment of Furniture, Bedding and Fabrics

Mattresses and box springs are treated with the pyrethrin insecticidal spray prepared as described as in Example 3. Each item is then completely covered with a vinyl or other impermeable mattress cover with zipper, e.g., Aller-Ease® (registered trademark of American Textile Company) mattress cover, available at retail stores.

Futon mattresses are removed from any outer covering (which laundered separately) and treated with spray from Example 3, then covered with a vinyl or similar impermeable mattress cover with zipper.

All mattresses and box springs were allowed to remain covered for at least 1 month. All infested fabric, i.e., clothing, draperies, bedding (sheets, comforters, futon covers, blankets, and bedspreads) are laundered and tumble dried at 114° F.

Upholstered furniture is sprayed on all surfaces, especially the bottom of sofas and chairs. Treatment to leather-upholstered items is restricted to the underside surfaces only to avoid any potential damage.

Example 5. Bed Bug Treatments and Follow-Up Observations

Individual apartment dwelling units of two multi-family buildings were inspected and evaluated for general condition and signs of bed bug infestation. Entire floor areas of each unit were completely treated with the spray formulations of Example 3. In addition, the perimeter of the baseboard/wall surface was treated in each room. Where possible, all rooms, including kitchens, bathrooms and closets were treated in this fashion. Hallways were treated similarly, including spraying upper molding on both sides of hallway, and in front of each doorway.

Following initial treatments, the treated areas were again inspected after a 10-14 day interval or a 24-28 day interval, and the degree of bed bug infestation was again evaluated. The results are summarized in Table 4, below.

TABLE 4

Assessment of Effectiveness of the Treated Areas

| Unit No. | Dwelling Type, flooring | Initial Condition | Initial Degree of infestation | Degree of Infestation after Treatment | No. of Eggs, Larvae or Live adults after Treatment | No. of Dead Adult Bed Bugs after Treatment |
|---|---|---|---|---|---|---|
| A. Building 1 (top floor) | | | | | | |
| A | Efficiency, carpet | Emptied by tenant | 3 | 0 | 0 | 0 |
| B | Efficiency, Hard floor | Cluttered | 3 | 0 (see Note) | | |
| C | Efficiency, Hard floor | Prepared by tenant | 2 | 0 | 0 | 0 |
| D | Efficiency, Hard floor | Very cluttered, soft items not laundered | 4 | 0 | 0 | 2 |
| E | Studio, Hard floor | Prepared by tenant | 1 | 0 | 0 | 1 |
| F | Studio, carpet | Inaccessible | | | | |
| G | Studio, Hard floor | Prepared but cluttered | 3 | 0 (see Note) | 0 | 0 |
| H | Studio, Hard floor | Empty | 1 | 0 | 0 | 0 |
| I | Studio | Inaccessible | | | | |
| J | Studio, carpet | Prepared by tenants | 3 | 0 | 0 | 0 |
| K | Studio, Hard floor | Prepared by tenant | 1 | 0 | 0 | 0 |
| L | Studio, carpet | Very cluttered | 3 | 0 | 0 | 0 |
| M | Studio, Hard floor | Cluttered | 3 | 0 | 0 | 0 |
| N | Studio | Inaccessible for treatment | 4 | | | |
| O | Studio | Inaccessible | | | | |
| P | Studio, carpet | Cluttered | 2 | Unit not accessible | | |
| Q | Studio, Hard floor | Prepared by tenant | 3 | Unit not accessible | | |
| R | Studio, carpet | Prepared by tenant | 2 | 0 | 0 | 1 |
| S | Studio, carpet | Prepared by tenants | 3 | 0 | 0 | 0 |
| Hallways | carpet | No clutter | 3 | 0 | 0 | 0 |
| B. Building 2 (Unit Name includes floor number) | | | | | | |
| 5C | Studio, Hardwood | Prepared by tenant | 1 | 0 | 0 | 0 |
| 5A | Efficiency, hardwood | Prepared by tenant | 2 | 0 | 0 | 0 |
| 4A | Efficiency, hardwood | Prepared by tenant | 3 | 0 | 0 | 0 |
| 3C | Efficiency | Inaccessible due to clutter | | | | |
| 3A | Studio, Hardwood | Prepared by tenant | 3 | 0 | 0 | 0 |
| 2C | Hardwood | Prepared by tenant | 3 | 0 | 0 | 0 |
| 2A | Efficiency, hardwood | Prepared by tenant | 1 | 0 (see Note) | 0 | 0 |

TABLE 4-continued

Assessment of Effectiveness of the Treated Areas

| Unit No. | Dwelling Type, flooring | Initial Condition | Initial Degree of infestation | Degree of Infestation after Treatment | No. of Eggs, Larvae or Live adults after Treatment | No. of Dead Adult Bed Bugs after Treatment |
|---|---|---|---|---|---|---|
| 3B | Studio, carpet | Inaccessible | 4 | | | |
| 4B | Studio, hardwood | Prepared by tenant | 3 | 0 | 0 | 1 |
| 4D | Studio, hardwood | Prepared by tenant | 3 | 0 | 0 | 0 |
| 4C | | Inaccessible | | | | |
| 2B | carpet | Prepared by tenant | 4 | 0 (See Note) | 0 | 0 |
| 5B | hardwood | Empty | 1 | 0 | 0 | 0 |
| Hallways | carpet | No clutter | 1 | 0 | 0 | 0 |

Note:
These Units were inspected 24-28 days after initial treatment.
Degree of Infestation Scale:
0 - None: No visible signs of bed bugs, including on mattresses and bedsprings. No tenant complaints.
1- Light: Tenant complains of bites, but no visible signs.
2 - Medium: Signs of infestations (live bugs, larvae or eggs, or fecal smears) and tenant complaints.
3 - Heavy: Heavy signs of infestations, including multiple sightings of live bugs, larvae or eggs. Tenant complaints (including that tenant is no longer sleeping on bed)
4 - Very Heavy: Very heavy signs of infestations in all accessible areas of the dwelling. Usually seen with Hoarders.

While the invention has been described with reference to particularly preferred embodiments and examples, those skilled in the art recognize that various modifications may be made to the invention without departing from the spirit and scope thereof.

All of the above U.S. patents, U.S. patent application publications, U.S. patent applications, foreign patents, foreign patent applications and non-patent publications referred to in this specification and/or listed in the Application Data Sheet are incorporated herein by reference, in their entirety.

What is claimed is:

1. A method of controlling bed bug infestations in an interior dwelling space, said method comprising the steps of
   1) cleaning and physically removing bed bugs in all life forms, including adults, larvae and eggs from surfaces and objects within the interior dwelling space, using a hot water extraction device, said device utilizing water that is heated to a temperature sufficient to kill or immobilize the bed bug adults, larvae and eggs, and to which is added a cleaning agent comprising from about 0.001 to about 5.0% of a first surfactant selected from the group consisting of a fluorochemical surfactant and a siloxane surfactant; and
   2) applying an arthropod control composition to said surfaces and objects within said interior dwelling space; said composition consisting essentially of a pyrethrin or a pyrethrin formulated with piperonyl butoxide and from about 0.001 to about 5.0% of a second surfactant selected from the group consisting of a fluorochemical surfactant and a siloxane surfactant.

2. The method of claim 1 wherein the cleaning agent added in step 1 comprises from about 0.001 to about 2.0% of the first surfactant, and the arthropod control composition in step 2 comprises consisting essentially of a pyrethrin or a pyrethrin formulated with piperonyl butoxide, and from about 0.001 to about 2.0% of a second surfactant.

3. The method of claim 1, wherein the first surfactant is a fluorochemical surfactant and the second surfactant is a siloxane surfactant.

4. The method of claim 3, wherein the first fluorochemical surfactant is a nonionic ethoxylated fluorosurfactant and the second siloxane surfactant is 3-(polyoxyethylene)propyl-heptamethyltrisiloxane or methyl(propylhydroxide, ethoxylated bis(trimethylsiloxy)silane.

5. A method of controlling bed bug infestations in an interior dwelling space, said method comprising the steps of
   1.) cleaning and physically removing bed bugs in all life forms, including adults, larvae and eggs from surfaces and objects within the interior dwelling space, using a hot water extraction device, said device utilizing water that is heated to a temperature of 137° F. to 150° F., and to which is added a cleaning agent comprising from about 0.001 to about 5.0% of a first surfactant selected from the group consisting of a fluorochemical surfactant and a siloxane surfactant; and
   2.) applying an arthropod control composition to said surfaces and objects within said interior dwelling space; said composition consisting essentially of a pyrethrin or a pyrethrin formulated with piperonyl butoxide, and from about 0.001 to about 5.0% of a second surfactant selected from the group consisting of a fluorochemical surfactant and a siloxane surfactant.

6. The method of claim 5 wherein the cleaning agent added in step 1 comprises from about 0.001 to about 2.0% of the first surfactant, and the arthropod control composition in step 2 consists essentially of a pyrethrin or a pyrethrin formulated with piperonyl butoxide, and from about 0.001 to about 2.0% of a second surfactant.

7. The method of claim 5, wherein the first surfactant is a fluorochemical surfactant and the second surfactant is a siloxane surfactant.

8. The method of claim 7 wherein the fluorochemical surfactant is a nonionic ethoxylated fluorosurfactant and the siloxane surfactant is 3-(polyoxyethylene)propylheptamethyltrisiloxane or methyl(propylhydroxide, ethoxylated bis(trimethylsiloxy)silane.

* * * * *